US008696902B2

(12) United States Patent
Ford et al.

(10) Patent No.: US 8,696,902 B2
(45) Date of Patent: Apr. 15, 2014

(54) HIGH PRESSURE CONNECT FITTING (75) Inventors: Douglas W. Ford, West Linn, OR (US); Robert DeLine, Corbett, OR (US)

(73) Assignee: Optimize Technologies, Inc., Oregon City, OR (US)

(*) Notice: Subject to any disclaimer, the term of this patent is extended or adjusted under 35 U.S.C. 154(b) by 144 days.

(21) Appl. No.: 11/971,834

(22) Filed: Jan. 9, 2008

(65) Prior Publication Data

US 2008/0237112 A1 Oct. 2, 2008

Related U.S. Application Data (60) Provisional application No. 60/884,186, filed on Jan. 9, 2007.

(51) Int. Cl.
*B01D 15/22* (2006.01)
*G01N 30/60* (2006.01)
*B01D 15/08* (2006.01)
*G01N 30/02* (2006.01)

(52) U.S. Cl.
USPC .......... 210/198.2; 210/656; 422/70; 73/61.53

(58) Field of Classification Search
USPC ................. 210/198.2; 285/361, 357
See application file for complete search history.

(56) References Cited

U.S. PATENT DOCUMENTS

| 221,794 A | 11/1879 | Dawson |
|---|---|---|
| 359,939 A | 3/1887 | Palmer |
| 397,904 A | 2/1889 | Folmer |
| 626,932 A | 6/1899 | Reed |
| 796,306 A | 8/1905 | Exley |
| 1,724,822 A | 8/1929 | Brown |
| 1,885,321 A | 11/1932 | Benn |
| 1,914,736 A | 6/1933 | Coutu |
| 2,204,392 A | 6/1940 | Arm |
| 2,349,081 A | 5/1944 | Douglass |
| 3,045,857 A | 7/1962 | Lineweber |
| 3,186,437 A | 6/1965 | Buono |
| 3,599,681 A | 8/1971 | Hall |
| 3,627,358 A | 12/1971 | Polston |
| 3,630,371 A | 12/1971 | Hrdina |
| 3,820,571 A | 6/1974 | Grier |
| 3,855,130 A | 12/1974 | Randau |
| 3,877,732 A | 4/1975 | Mohaupt |
| 3,878,099 A | 4/1975 | Ogle |
| 3,926,187 A | 12/1975 | Iglesias |
| 3,958,898 A | 5/1976 | Abrahams |
| 4,026,803 A | 5/1977 | Abrahams |
| 4,084,718 A | 4/1978 | Wadsworth |
| 4,093,550 A | 6/1978 | Stahl |

(Continued)

*Primary Examiner* — Katherine Zalasky
(74) *Attorney, Agent, or Firm* — Christensen O'Connor Johnson Kindness PLLC (57) ABSTRACT

An analytical instrument fitting assembly for coupling first and second analytical fluid conduits is provided. The fitting assembly includes a first fitting defining a central passage adapted to receive a first fluid conduit defining an internal diameter of no greater than 0.040 inch and a second fitting. The second fitting defines a central passage extending between first and second ends and is in fluid communication with the first fitting. A separation device is disposed within a central passages of the first and second fittings to selectively separate liquids passing therethrough. The fitting assembly further includes a retractable end fitting having a housing, a tube extending within the housing, and a biasing member. Selective positioning of the tube within the housing minimizes dead space between the tube and the second end.

23 Claims, 10 Drawing Sheets

(56) References Cited

U.S. PATENT DOCUMENTS

| | | | |
|---|---|---|---|
| 4,168,235 | A | 9/1979 | Guillemin |
| 4,173,363 | A | 11/1979 | Stearns |
| 4,181,853 | A | 1/1980 | Abu-Shumays |
| 4,187,177 | A | 2/1980 | Stahl |
| 4,228,007 | A | 10/1980 | Rausch |
| 4,281,679 | A | 8/1981 | Stearns |
| 4,283,280 | A | 8/1981 | Brownlee |
| 4,311,440 | A | 1/1982 | Eberhardt |
| 4,313,828 | A | 2/1982 | Brownlee |
| 4,389,313 | A | 6/1983 | Charney |
| 4,394,263 | A | 7/1983 | Dosch |
| 4,451,363 | A | 5/1984 | Brownlee |
| 4,451,364 | A | 5/1984 | Higgins |
| 4,451,365 | A | 5/1984 | Sattler |
| 4,457,846 | A | 7/1984 | Munk |
| 4,476,017 | A | 10/1984 | Scharff |
| 4,512,899 | A | 4/1985 | Goodnight, Jr. |
| 4,522,715 | A | 6/1985 | Walters |
| 4,529,167 | A | 7/1985 | Harrison |
| RE31,974 | E | 8/1985 | Brownlee |
| 4,541,452 | A | 9/1985 | Paradis |
| 4,586,732 | A | 5/1986 | Anderson, Jr. |
| 4,587,014 | A | 5/1986 | America |
| 4,632,433 | A | 12/1986 | Kimura |
| 4,655,917 | A | 4/1987 | Shackelford |
| 4,648,635 | A | 5/1987 | Juhling |
| 4,662,396 | A | 5/1987 | Avnon |
| 4,708,782 | A | 11/1987 | Andresen |
| 4,732,672 | A | 3/1988 | Kiang |
| 4,737,284 | A | 4/1988 | Hauke |
| 4,740,298 | A | 4/1988 | Andresen |
| 4,765,890 | A | 8/1988 | Tehrani |
| 4,792,396 | A | 12/1988 | Gundelfinger |
| 4,793,920 | A | 12/1988 | Cortes |
| 4,819,684 | A | 4/1989 | Zaugg |
| 4,842,592 | A | 6/1989 | Caggiani |
| 4,861,473 | A | 8/1989 | Shackelford |
| 4,876,005 | A | 10/1989 | America |
| 4,882,047 | A | 11/1989 | Shalon |
| 4,882,063 | A | 11/1989 | Allington |
| 4,888,112 | A | 12/1989 | Kronwald |
| 4,894,152 | A | 1/1990 | Colvin, Jr. |
| 4,991,820 | A * | 2/1991 | Kohn et al. ................ 251/149.5 |
| 4,994,180 | A | 2/1991 | Sims |
| 5,037,544 | A | 8/1991 | Snyder |
| 5,087,086 | A * | 2/1992 | Snedeker ...................... 285/361 |
| 5,110,558 | A | 5/1992 | Romer |
| 5,169,522 | A | 12/1992 | Shalon |
| 5,172,942 | A | 12/1992 | Dillmann |
| 5,188,730 | A | 2/1993 | Kronwald |
| 5,194,225 | A | 3/1993 | Muller |
| 5,227,059 | A | 7/1993 | Shepherd |
| 5,246,577 | A | 9/1993 | Fuchs |
| 5,439,593 | A | 8/1995 | Price |
| 5,525,303 | A | 6/1996 | Ford |
| 5,572,920 | A * | 11/1996 | Kennedy et al. ................ 92/128 |
| 5,911,954 | A | 6/1999 | Ford |
| 6,000,916 | A * | 12/1999 | Martin et al. ................ 417/360 |
| 6,095,572 | A | 8/2000 | Ford |
| 6,494,500 | B1 | 12/2002 | Todosiev |
| 6,730,218 | B2 * | 5/2004 | Bozenmayer ................ 210/232 |

\* cited by examiner

HIGH PRESSURE CONNECT FITTING

CROSS-REFERENCE TO RELATED APPLICATION

This application claims the benefit of U.S. Provisional Patent Application No. 60/884,186, filed Jan. 9, 2007.

TECHNICAL FIELD

The disclosed subject matter relates generally to fittings used to connect miniature conduits, and particularly to connectors for fluid transfer in analytical instruments.

BACKGROUND

Numerous types of equipment used for the analysis or purification of chemical compounds utilize miniature fluid conduits, such as metallic tubing, through which liquid samples pass. An analytical technique, such as liquid chromatography, uses a column (conduit) packed with a packing material in order to analyze and identify chemical properties of certain fluids. For example, an analyte may be introduced into one end of the column, and a carrier fluid then run through the column. The length of time that the analyte is retained within the column can enable analysis and identification of the analyte. A popular form of liquid chromatography is High Performance Liquid Chromatography (HPLC) in which the sample is pumped through the column under an elevated pressure, typically at 300 to 6,000 psi. Another, relatively newer liquid chromatography form is Ultrahigh Pressure Liquid Chromatography (UHPLC) in which system pressure extends upward to 1400 bar or 20,000 psi. Both HPLC and UHPLC are examples of analytical instrumentation that utilize fluid transfer at elevated pressures.

Liquid chromatography systems, such as HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the HPLC column itself; and a detector that analyzes the carrier fluid as it leaves the column. These various components may typically be connected by a miniature fluid conduit, such as metallic or polymeric tubing, usually having an internal diameter of 0.003 to 0.040 inch.

All of these various components and lengths of tubing are typically interconnected by threaded fittings. Fittings for connecting various components and lengths of tubing are disclosed in prior patents, for example, U.S. Pat. Nos. 5,525,303; 5,730,943; and 6,095,572, the disclosures of which are herein all incorporated by reference herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. While hand-tightened threaded fittings eliminate the need for wrenches or other tools these fittings typically could not stand up to the extreme pressures of HPLC or UHPLC.

SUMMARY

This summary is provided to introduce a selection of concepts in a simplified form that is further described below in the Detailed Description. This summary is not intended to identify key features of the claimed subject matter, nor is it intended to be used as an aid in determining the scope of the claimed subject matter.

An analytical instrument fitting assembly for coupling first and second analytical fluid conduits is provided. The fitting assembly includes a first fitting defining a central passage adapted to receive a first fluid conduit defining an internal diameter of no greater than 0.040 inch and a second fitting. The second fitting defines a central passage extending between first and second ends and is in fluid communication with the first fitting.

In one embodiment, the fitting assembly also includes a packed bed disposed within the central passages of the first and second fittings. Such a packed bed includes a body at least partially filled with a separating media and a first seal disposed on a first end of the body to seal the filter material within the body. The fitting assembly also includes a retractable end fitting at least partially disposed within the second end of the second fitting. The retractable end fitting includes a housing, a tube extending within the housing, and a biasing member extending between the housing and a washer disposed on the tube to allow selective positioning of the tube within the housing relative to the second end of the second fitting to minimize dead space between the tube and the second end.

DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION

Figure 1:
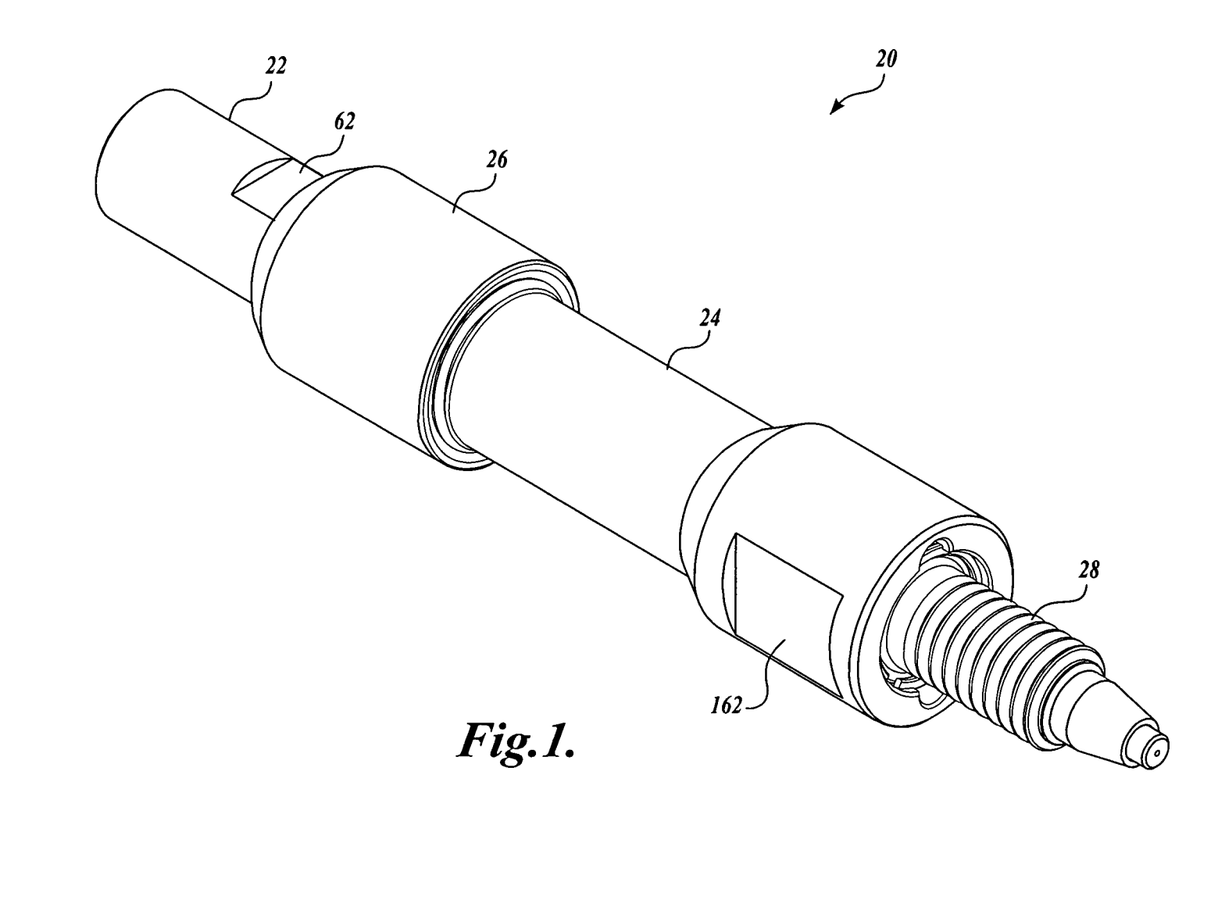
FIG. 1 is an isometric view of an exemplary embodiment of a high pressure connect fitting according to the present disclosure.
Figure 2:
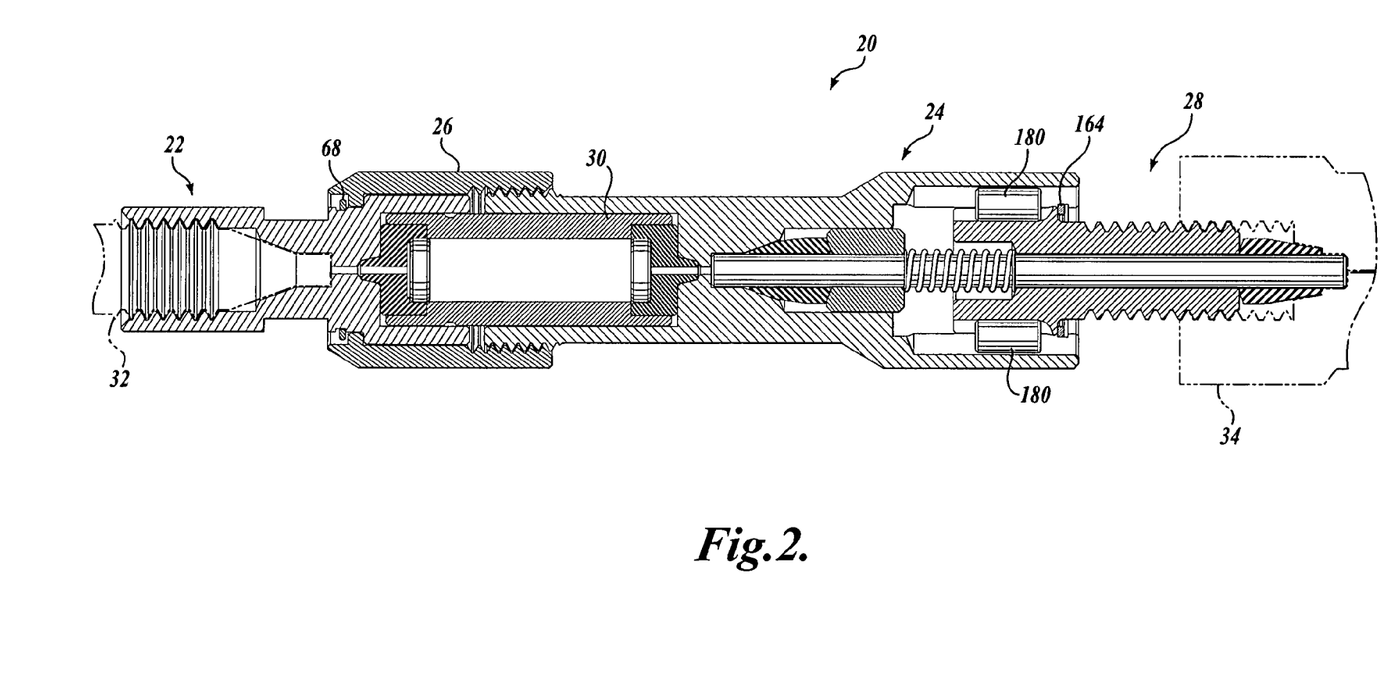
FIG. 2 is a cross-sectional view of the high pressure connect fitting shown in FIG. 1.

A first exemplary embodiment of a high pressure connect fitting assembly 20 is shown in FIGS. 1 and 2. The high pressure connect fitting 20 includes a first fitting 22 rotatably coupled to a second fitting 24 with a lock ring 26 or coupler. A retractable end fitting 28 is slidingly secured to the end of the second fitting 24 opposite the first fitting 22. The fitting assembly 20 serves as a connector between various miniature fluid conduit terminals, such as, for example, a fluid line in 32 and a column inlet port 34, both shown in phantom in FIG. 2.

Figure 3:
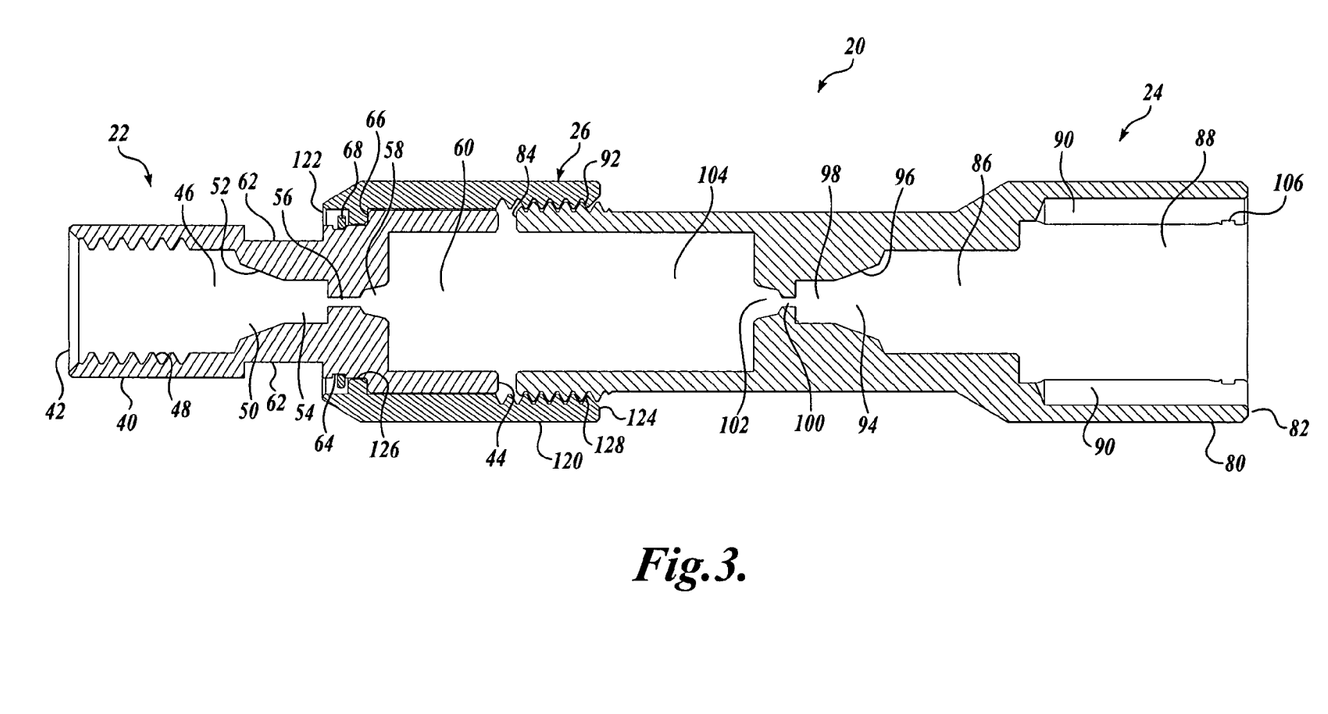
FIG. 3 is a cross-sectional view of a first fitting and a second fitting of the high pressure connect fitting shown in FIG. 1.

As best shown in FIG. 3, the first fitting 22 is preferably of unitary construction and includes a tubular body 40 having a proximal end 42 and a distal end 44. A central passage 46 extends from the proximal end 42 to the distal end 44 of body 40. A portion of the central passage 46 includes a threaded portion 48 configured to engage an externally threaded mating coupling of a miniature fluid conduit.

The central passage 46 narrows in diameter at its distal terminus to form a tapered chamber 50 that extends from the internally threaded portion 48 toward the distal end 44 of the first fitting 22. The tapered chamber 50 includes a frustoconical sealing surface 52 that seals against a conventional ferrule received coaxially from the coupling of the miniature fluid conduit. The central passage 46 further narrows to form a cylindrical chamber 54 that extends distally from the tapered chamber 50. The cylindrical chamber 54 forms a "tube stop" that closely and fully receives the tip of a coupling of a miniature fluid conduit, as described in greater detail below.

The cylindrical chamber 54 further narrows to form a passage 56 extending from the cylindrical chamber 54 to a sealing recess 58 located on the proximal end of a larger annular recess 60 formed in the distal end 44 of the first fitting 22. The passage 56 is sized to correspond to the internal diameter of the fluid conduit 32, which is typically in the range of 0.005 to 0.040 inch. When the fluid conduit 32 is coupled to the first fitting 22, the tip of the fluid conduit 32 contacts the end surface of the cylindrical chamber 54. Thus, a "zero-dead volume" connection is created between the fluid conduit and the first fitting 22 so that fluid discharged from the fluid conduit 32 can only enter the small diameter passage 56 in the first fitting 22.

As shown in FIGS. 1 and 3, the outer surface of the first fitting 22 includes diametrically opposed flat surfaces 62 to allow engagement a wrench or similar tool, if desired, to rotate the first fitting 22 or to prevent the first fitting from rotating as the fluid conduit 32 is coupled or decoupled to the first fitting 22. In an alternate embodiment, the first fitting 22 has a knurled outer surface to facilitate gripping the first fitting 22 while coupling or decoupling the fluid conduit.

The outer surface of the first fitting 22 includes an annular groove 64 between the flat surfaces 62 and the distal end 44 of the first fitting 22. On the distal side of the annular groove 64, the outer diameter of the first fitting 22 increases to define a shoulder 66 that faces the proximal end 42 of the first fitting.

Figure 5:
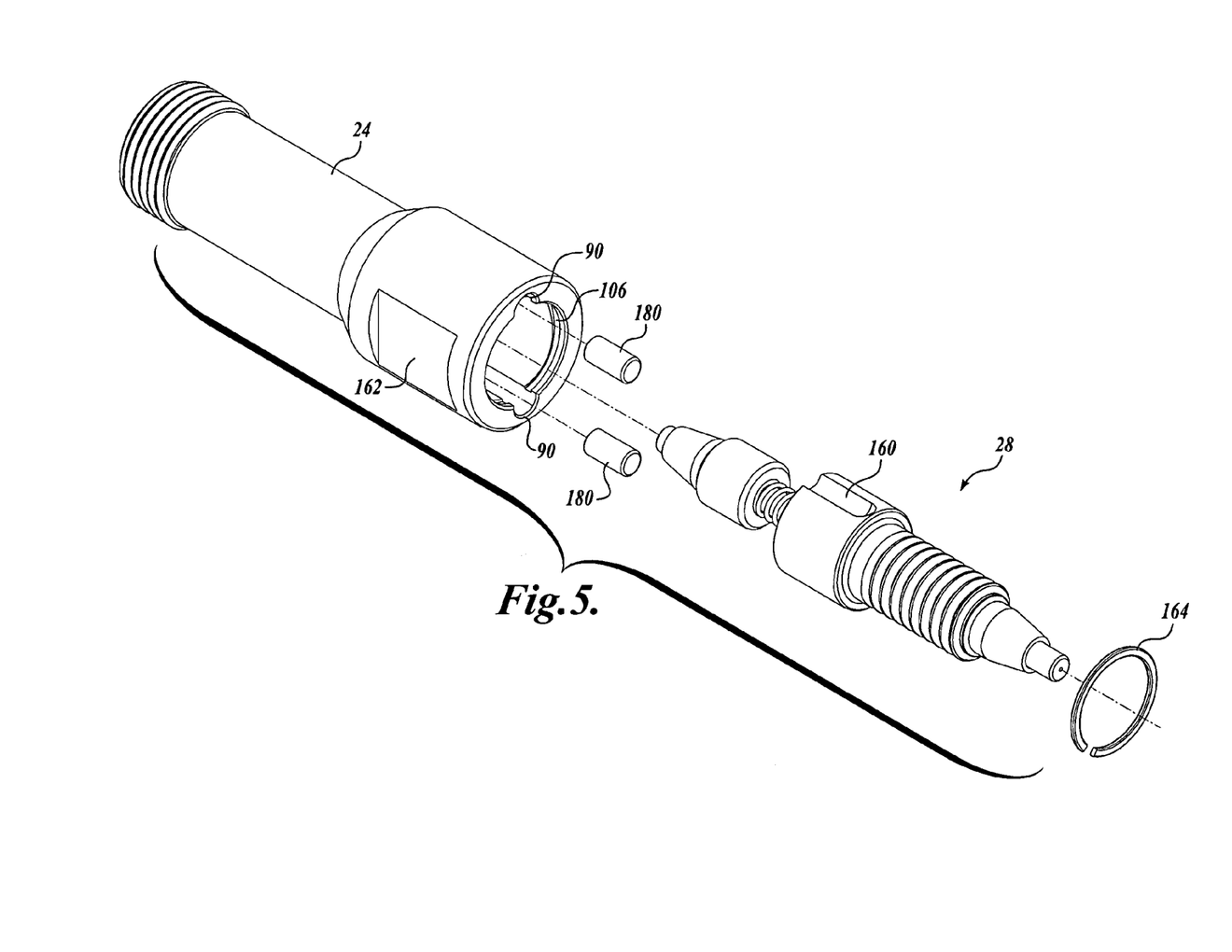
FIG. 5 is an partial isometric exploded view of the high pressure connect fitting shown in FIG. 1.

Still referring to FIG. 3, the second fitting 24 includes a tubular body 80 with a proximal end 82 and a distal end 84. A central passage 86 extends from the proximal end 82 to the distal end 84 of the body 80. The proximal end of central passage 86 terminates in an annular recess 88 adapted to receive a retractable end fitting 28 (described later). As best shown in FIGS. 3 and 5, diametrically opposed longitudinal grooves 90 extend along the surface of the annular recess 88. The annular recess 88 also includes an annular groove 106 extending circumferentially around the recess 88 near the proximal end 82 of the second fitting 24. The second fitting 24 further includes an external threaded surface 92 formed on the distal end 84 thereof.

The central passage 86 narrows in diameter at its distal terminus to form a tapered chamber 94. The tapered chamber 94 is defined by a frustoconical sealing surface 96 that seals against a conventional ferrule included on the end of the retractable end fitting 28 shown in FIG. 4. Referring back to FIG. 3, a cylindrical chamber 98 extends from the tapered chamber 94 toward the distal end 84 of the second fitting 24. The cylindrical chamber 98 forms a "tube stop" that closely and fully receives the distal tip of the retractable end fitting 28. The cylindrical chamber 98 further narrows to form a passage 100 that extends from the cylindrical chamber 98 to a tapered sealing recess 102 located at the proximal end of an annular recess 104 formed in the distal end 44 of first fitting 22. The passage 100 is sized to correspond to the internal diameter of the distal tip of the retractable end fitting 28 in order to form a zero-dead volume connection therewith.

As best shown in FIGS. 1 and 5, the outer surface of the second fitting 24 includes flat surfaces 162 to allow engagement a wrench or similar tool, if desired, to rotate the second fitting 24 as the high pressure connect fitting 20 is coupled or decoupled to a downstream system component 34. In an alternate embodiment, the second fitting 24 has a knurled outer surface to facilitate gripping the second fitting 24 while coupling or decoupling the high pressure connect fitting 20 to the downstream system component 34.

Still referring to FIG. 3, the lock ring 26 has a tubular body 120 with a proximal end 122 and a distal end 124. An annular protrusion 126 extends radially inward from the inner surface of the lock ring 26 at the proximal end 122 thereof. The interior portion of the lock ring 26 also includes a threaded surface 128 at the distal end 124 of the lock ring 26. The internal threaded surface 128 of the lock ring 26 is configured to threadedly engage the external threaded surface 92 of the second fitting 24. Specifically, the lock ring 26 is adapted to connect the first and second fittings 22 and 24 by application of a torque, or coupling force, to the lock ring 26 preferably, but not necessarily, without the use of a mechanical hand tool, such as a wrench. In one embodiment, the range of the coupling force is substantially between 0.1-5.0 inch-pounds to rotate the lock ring 26 less than 90° from an unlocked position wherein the first and second fittings are detachable from the lock ring 26. As an example, the lock ring 26 a coupling force of substantially between 0.5-2.0 inch-pounds to rotate the lock ring 26 substantially between 45°-60° from the unlocked position.

The lock ring 26 engages the first fitting 22 and the second fitting 24 in order to couple the first fitting 22 to the second fitting 24. The distal end 44 of the first fitting 22 is positioned within the interior portion of the lock ring 26 so that the distal side of the annular protrusion 126 of the lock ring 26 abuts the proximal side of the internal shoulder 66 of the first fitting 22. A snap ring 68 is positioned circumferentially around the body of the first fitting 22 and is retained in the annular groove 64 in the first fitting 22. With the snap ring 68 so located, the annular protrusion 126 of the first fitting 22 is retained between the snap ring 68 and the internal shoulder 64 of the first fitting 22, thereby restraining the first fitting 22 against translational movement relative to the lock ring 26. At the same time, the first fitting 22 is unrestrained against rotation relative to the lock ring 26.

The second fitting 24 is secured to the lock ring 26 by engaging the threads 92 on the distal end 44 of the second fitting 24 with the internal threaded surface 128 located at the distal end 124 of the lock ring 26. Thus, with the first and second fittings 32 and 34 secured to the lock ring 26 in the illustrated manner, the first fitting 22 is coupled to the second fitting 24. The described coupling restrains the first fitting 22 from translational movement relative to the second fitting 24, but allows rotational movement to occur therebetween.

Figure 4:
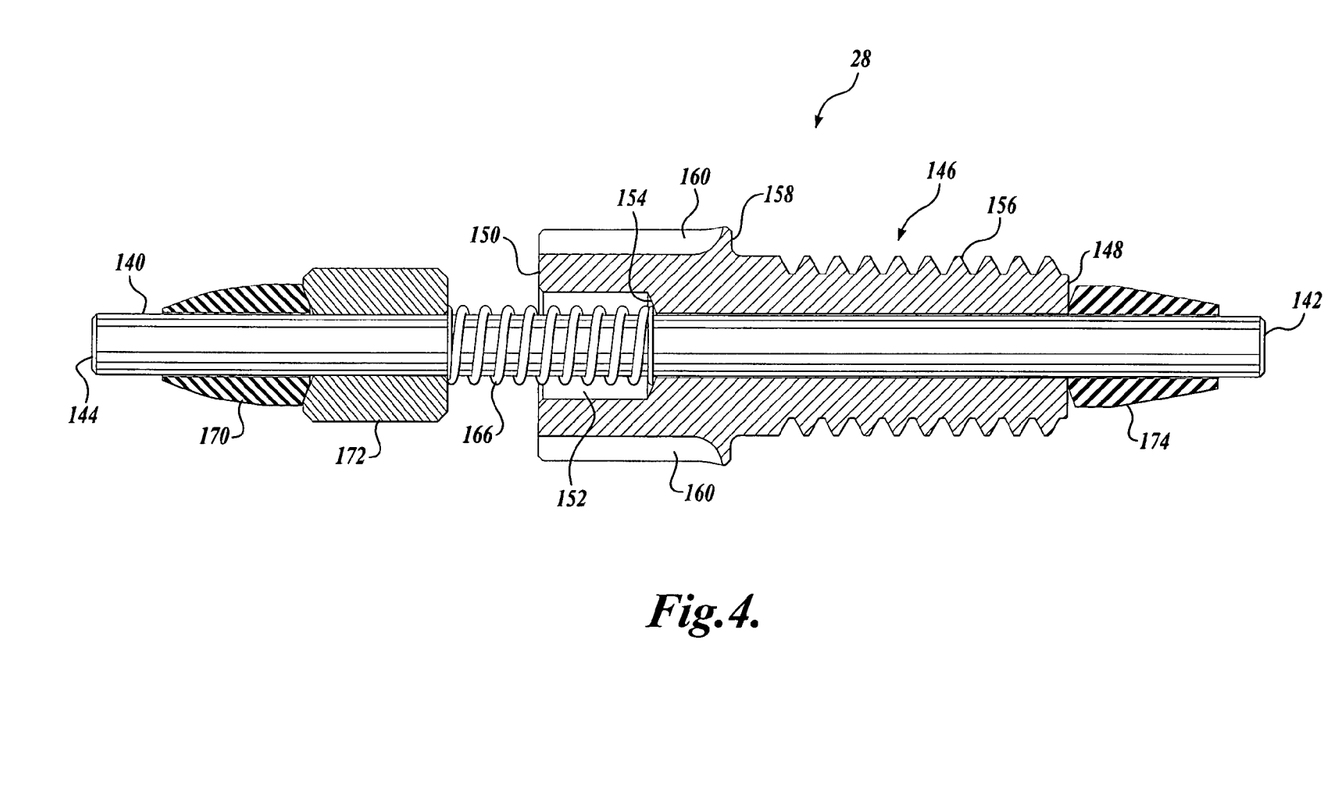
FIG. 4 is a cross-sectional view of a retractable end fitting of the high pressure connect fitting shown in FIG. 1.

As may be seen best by referring to FIG. 4, the retractable end fitting 28 includes a tube 140 having a proximal end 142 and a distal end 144. The tube 140 is disposed within a center portion of a threaded fitting 146, or body, which has a proximal end 148 and a distal end 150, so that the proximal and distal ends 142 and 144 of the tube 140 extend from the proximal and distal ends 148 and 150, respectively, of the threaded fitting 146.

The threaded fitting 146 has external threads 156 sized to threadedly engage the internal threads of a corresponding mating instrument inlet or outlet shown in FIG. 2. The threaded fitting 146 includes a shoulder 158 facing the proximal end 148 of the threaded fitting 146. A generally cylindrical recess 152 is located on the distal end 150 of the threaded fitting 146. As shown in FIG. 4, the recess defines an interior shoulder 154 within the fitting 146.

Still referring to FIG. 4, a ferrule 170 is slidably mounted on the distal end 144 of the tube 140 so that the distal end 144 of the tube 140 extends from the tapered end of the ferrule 170. A support washer 172 is slidably mounted to the distal end 144 of the tube opposite the tapered end of the ferrule 170, i.e. between the ferrule 170 and the threaded fitting 146. A helical spring 166, or biasing member, is positioned coaxially around the tube 140 between the support washer 172 and the distal end 150 of the threaded fitting 146. One end of the spring 166 engages the support washer 172 and the other end of the spring 166 engages the shoulder 154 located within the recess 152 at the distal end 150 of the threaded fitting 146 to provide a force that biases the support washer 172 and ferrule 170 away from the threaded fitting 146.

A second ferrule 174 is slidingly mounted to the proximal end 142 of the tube 140 so that the proximal end 142 of the tube 140 extends from the tapered end of the ferrule 174. The end of the ferrule 174 opposite the tapered end abuts the proximal end 148 of the threaded fitting 146.

The retractable end fitting 28 is slidably coupled to the second fitting 24 so that the retractable end fitting 28 extends from the proximal end 82 of the second fitting 24, but is capable of at least partially retracting within the second fitting 32. Referring to FIGS. 2-5, the retractable end fitting 28 is disposed within the annular recess 88 in the second fitting 24 so that the distal end 144 of the end fitting tube 140 is positioned within the cylindrical chamber 98 of the second fitting 24. The support washer 172 is located within and engages the passage 86 in the second fitting 24 to provide further support to the distal end 144 of the tube 140. The helical spring 166 biases the support washer 172 toward the distal end 144 of the tube 140, which in turn biases the tapered end of the ferrule 170 into the tapered chamber 94 of the second fitting 24. The ferrule 170 engages the sealing surface 96 of the tapered chamber 94 to form a seal therebetween. Because the tube 140 is capable of sliding relative to the ferrule 170 and the support washer 172, dead space between the distal end 144 of the tube 140 and the small diameter passage 100 at the end of the cylindrical chamber 98 is eliminated.

The retractable end fitting 28 is contained within the annular recess 88 of the second fitting 24 with a snap ring 164. As best shown in FIGS. 2 and 3, the snap ring 164 is positioned within the groove 106 in the annular recess 88 of the second fitting 24 so that the snap ring 64 engages the shoulder 158 of the threaded fitting 146, thereby keeping the threaded fitting 146 at least partially contained within the annular recess 88. The helical spring 166 provides a force at the distal end 150 of the threaded fitting 146 to bias the distal end 150 of the threaded fitting 146 toward the proximal end 82 of the second fitting 24. Thus, the shoulder 150 of the threaded fitting 146 maintains contact with the snap ring 164, i.e. the retractable end fitting 28 remains fully extended, unless or until a force is applied to the threaded fitting 146 sufficient to overcome the biasing force of the helical spring 166, which results in the threaded fitting 146 retracting into the annular recess 88 of the second fitting 24.

As best shown in FIGS. 2 and 5, a pair of pins 180 are positioned between the second fitting 24 and the retractable end fitting 28. Each pin 180 is partially disposed within one of the axial grooves 90 in the second fitting 24, and also within one of the axial grooves 160 in the retractable end fitting 28. The engagement of the pins 180 with the grooves 90 and 160 of the second fitting 24 and the retractable end fitting 28 prevent rotation of the retractable end fitting 28 relative to the second fitting 24. Although the illustrated embodiment is shown with two pins 180, it will be appreciated that any suitable number of pins can be used, including, for example, one pin or three or more pins.

As previously noted, the threaded fitting 146 and the ferrule 174 of the retractable end fitting 28 are capable of sliding relative to the tube 140. As a result, the amount by which the proximal end 142 of the tube 140 extends from the tapered end of the ferrule 174 changes as necessary when the high pressure connect fitting 20 is coupled to a corresponding mating instrument inlet or outlet 34 in order to eliminate dead space between the proximal end of the tube 142 and the corresponding mating instrument inlet or outlet 34. This creates a zero dead volume attachment.

Figure 6:
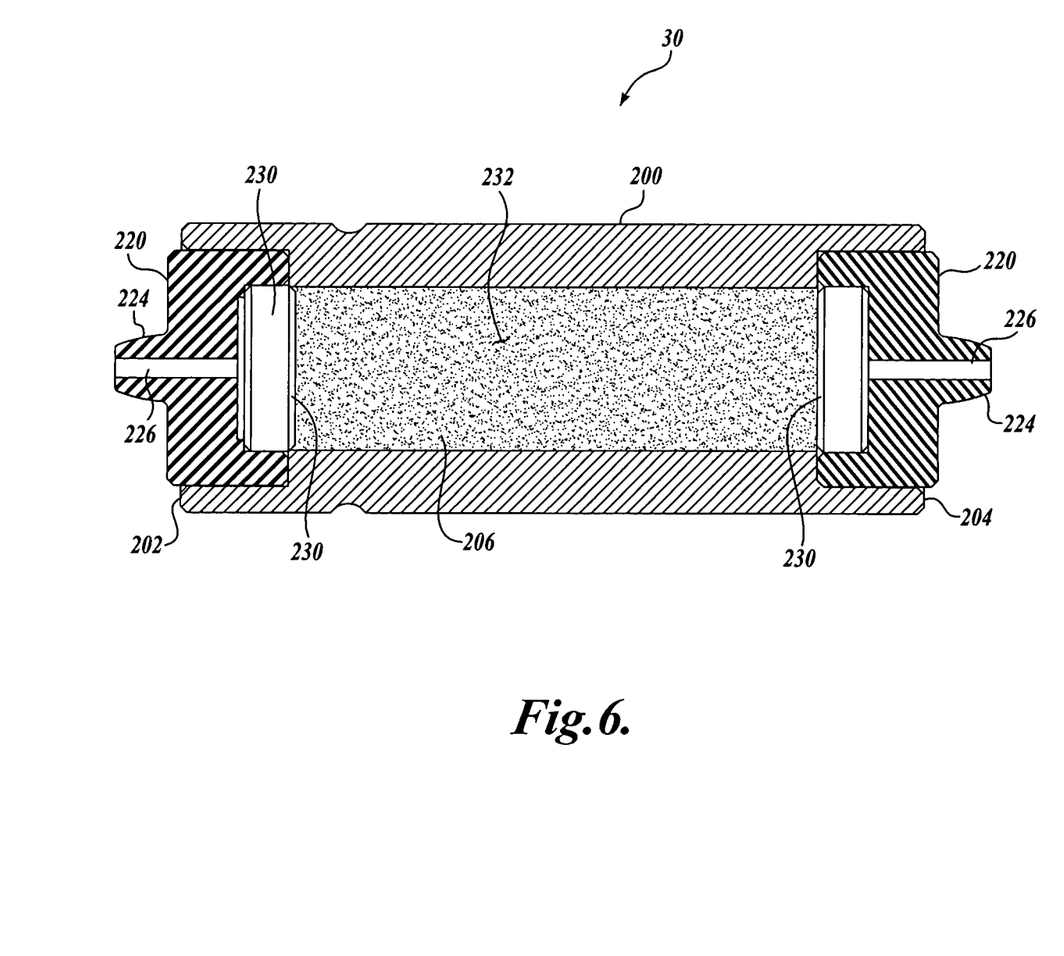
FIG. 6 is a cross-sectional view of a packed bed of the high pressure connect fitting shown in FIG. 1.
Figure 7:
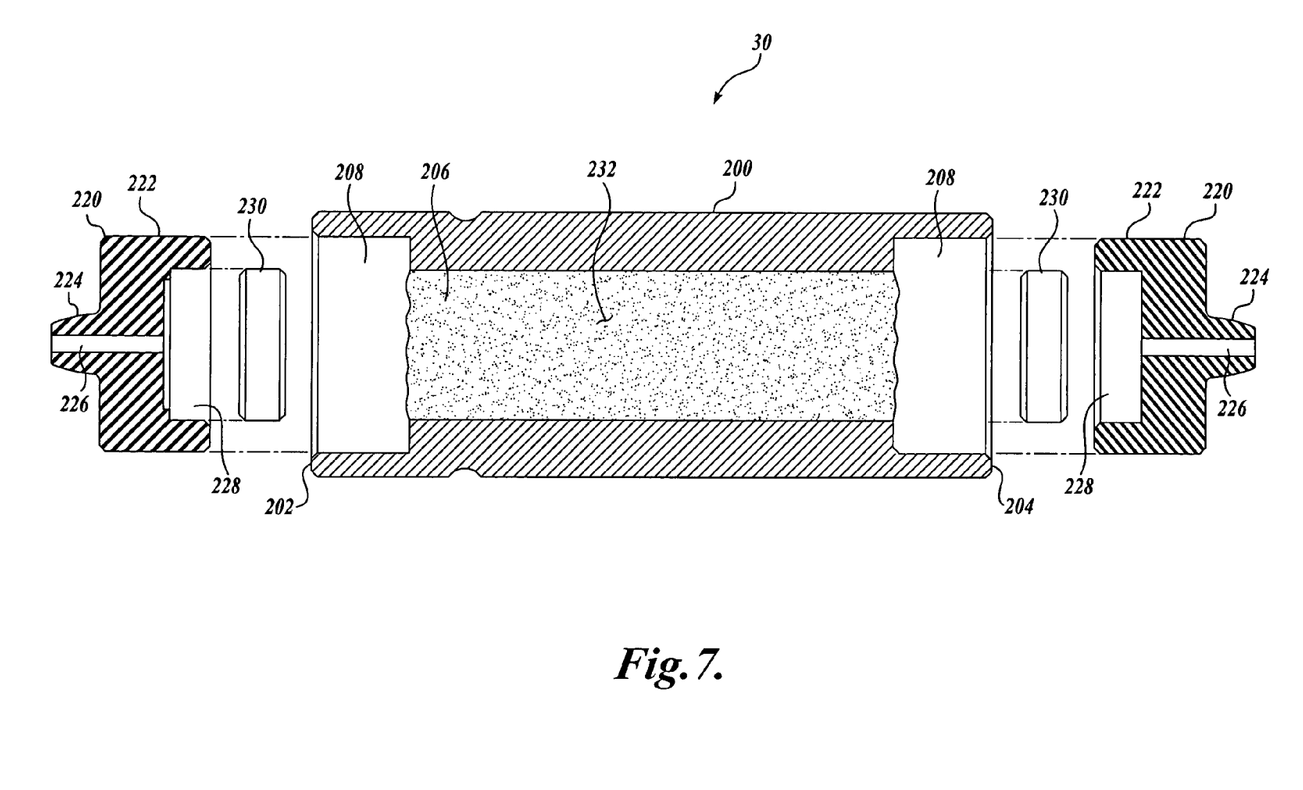
FIG. 7 is an exploded cross-sectional view of the packed bed shown in FIG. 6.

Referring back to FIGS. 2 and 3, a packed bed 30 is disposed within the cavity formed by the annular recess 60 of the first fitting 22 and the annular recess 104 of the second fitting 24 when the first and second fittings 22 and 24 are coupled together with the lock ring 26. As best shown in FIGS. 6 and 7, the packed bed 30 has a generally cylindrical body 200 with an input end 202, an output end 204, and a central passage 206 extending therethrough. The input end 202 and output end 204 of the body 200 each includes an annular recess 208 in which a seal 220 is disposed. The seals 220 at the input end 202 and the output end 204 of the body 200 are identical both in configuration and operation.

The seal 220 is preferably manufactured from a polymer, such as polyetheretherketone ("PEEK"). The seal 220 includes a body portion 222, an integrally formed tip 224, and a centrally extending passage 226. The body 222 of the seal 220 is sized and configured to fit within the annular recess 208 at the input end 202 or the output end 204 of the packed bed body 200. A porous plug 230 has an annular body sized to fit within the annular recess 228 in the seal 220. The porous plug 230 is formed from a material that selectively allows certain materials to pass through the plug 230, while restricting the passage of other materials.

A packing material (or separating media) 232 is disposed within the passage 206 of the packed bed 30. The packing material 232 may be a particulate packing material, through which particles greater than a predetermined size are prevented from passing. Alternately, the packing material may be a chemical packing material, such as a selectively absorbent or adsorbent packing material that filters out substances having specific chemical properties. It should be appreciated that any known packing material suitable for selectively filtering fluids passing therethrough can be included without departing from the scope of the disclosure.

With a seal 220 positioned in the annular recess 208 at each end of the packed bed body, and a porous plug 230 disposed within the annular recess 228 of each seal 220, the packing material 232 is contained within the packed bed 30. A fluid to be filtered is introduced to the input end 202 of the packed bed 30 and passes through the seal 220 and the porous plug 230. As the fluid passes through the packed bed 30, undesired elements are adsorbed by the packing material 232, and the filtered fluid exits the packed bed 30 through the porous plug 230 and the seal 220 at the output end 204 of the packed bed 30.

As seated within the cavity formed by the annular recess 60 in the first fitting 22 and the annular recess 104 in the second fitting 24, the seals 220 of the packed bed 30 engage the sealing recess 58 and 102 of the first fitting 22 and the second fitting 24, respectively. The engagement of the seal 220 with the first fitting 22 is similar to the engagement of the seal 220 with the second fitting 34. Accordingly, the engagement of one seal 220 with the second fitting 24 will be described with the understanding that the description is applicable to the engagement of the other seal 220 with the first fitting 22.

Figure 8:
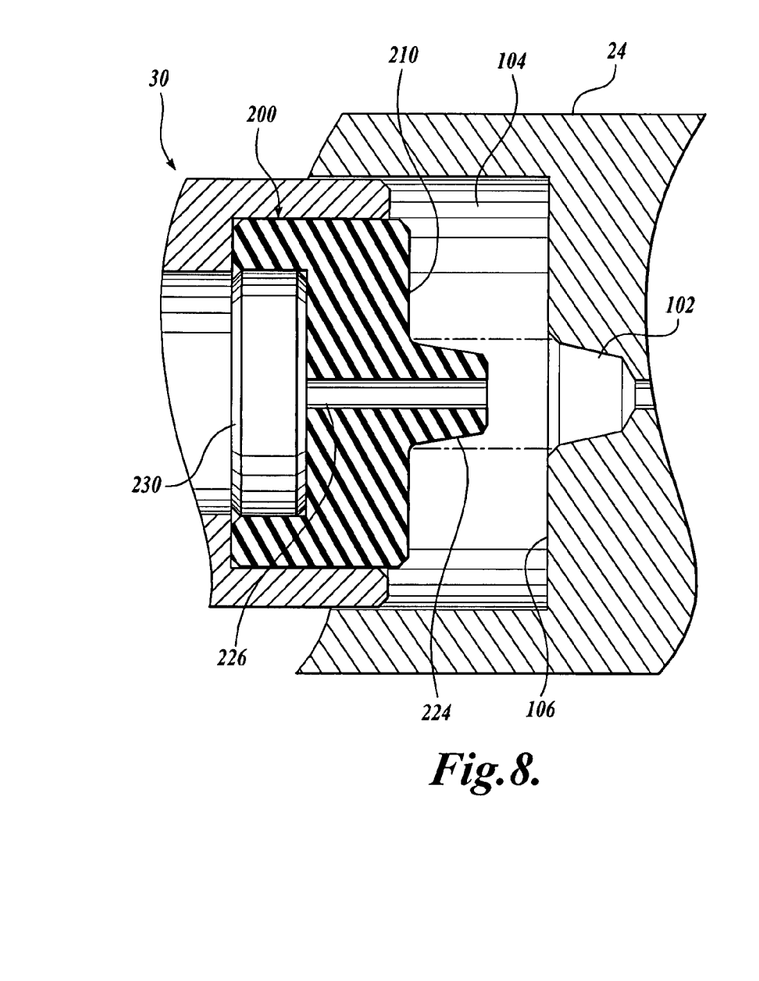
FIG. 8 is a partial exploded cross-sectional view of the packed bed and the second fitting of the high pressure connect fitting shown in FIG. 1.
Figure 9:
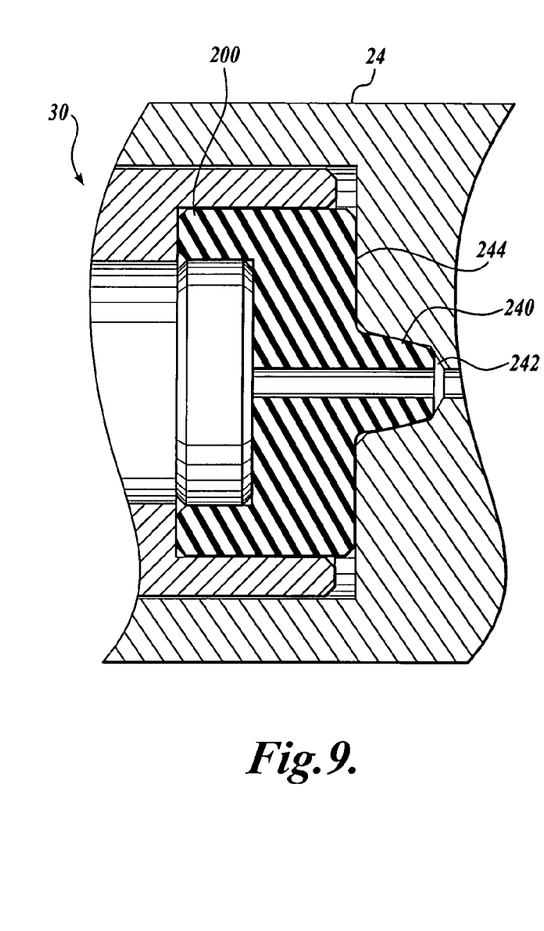
FIG. 9 is a partial cross-sectional view of the packed bed and the second fitting of the high pressure connect fitting shown in FIG. 8.

Referring to FIGS. 8 and 9, as the seal 200 engages the second fitting 24, the tip 224 of the seal 200 contacts the walls of the tapered sealing cavity 102 to form a primary seal 240. The volume of space between the very end of the tip 224 and the end of the sealing cavity 102 defines a dead space 242. As the seal 220 is axially compressed within the annular recess 104, the tip 224 not only engages the walls of the tapered sealing cavity 102 to form the primary seal, but also deforms to occupy space otherwise associated with the dead space 242. As, the tip 224 of the seal 200 engages the tapered sealing cavity 102, the end face 210 of the seal 220 compresses against the end 108 of the annular recess 104 to form a secondary seal 244 extending radially around the tip 224 of the seal 200.

In addition to providing a secondary seal 24, contact between the end face 210 of the seal 220 and the end 108 of the annular recess 104 serves to limit the deformation of the seal tip 224. As previously described, the second fitting 24 is coupled to the first fitting 22 by threadedly engaging the second fitting 24 to a lock ring 26 that is also coupled to the first fitting 22. As the lock ring 26 is rotated relative to the second fitting 24 the distal end 84 of the second fitting 24 is drawn toward the distal end 44 of the first fitting 22. As a result, the overall length of the cavity formed by the annular recess 60 in the first fitting 22 and the annular recess 104 in the second fitting 24 is reduced. Absent the contact between the end face 210 of the seal 220 and the end 108 of the annular recess 104, over tightening the lock ring 26 would force the tip 224 of the seal 220 into the sealing recess 102 to the point where deformation of the tip would potentially block the passage 226 extending through the seal. However, engagement of the end face 210 of the seal 220 with the end 108 of the annular recess 104 limits the amount by which the length of the cavity can be reduced. As a result, the amount by which the tip 224 extends into the sealing recess 102, and thus the deformation of the tip 244, is limited.

Figure 10:
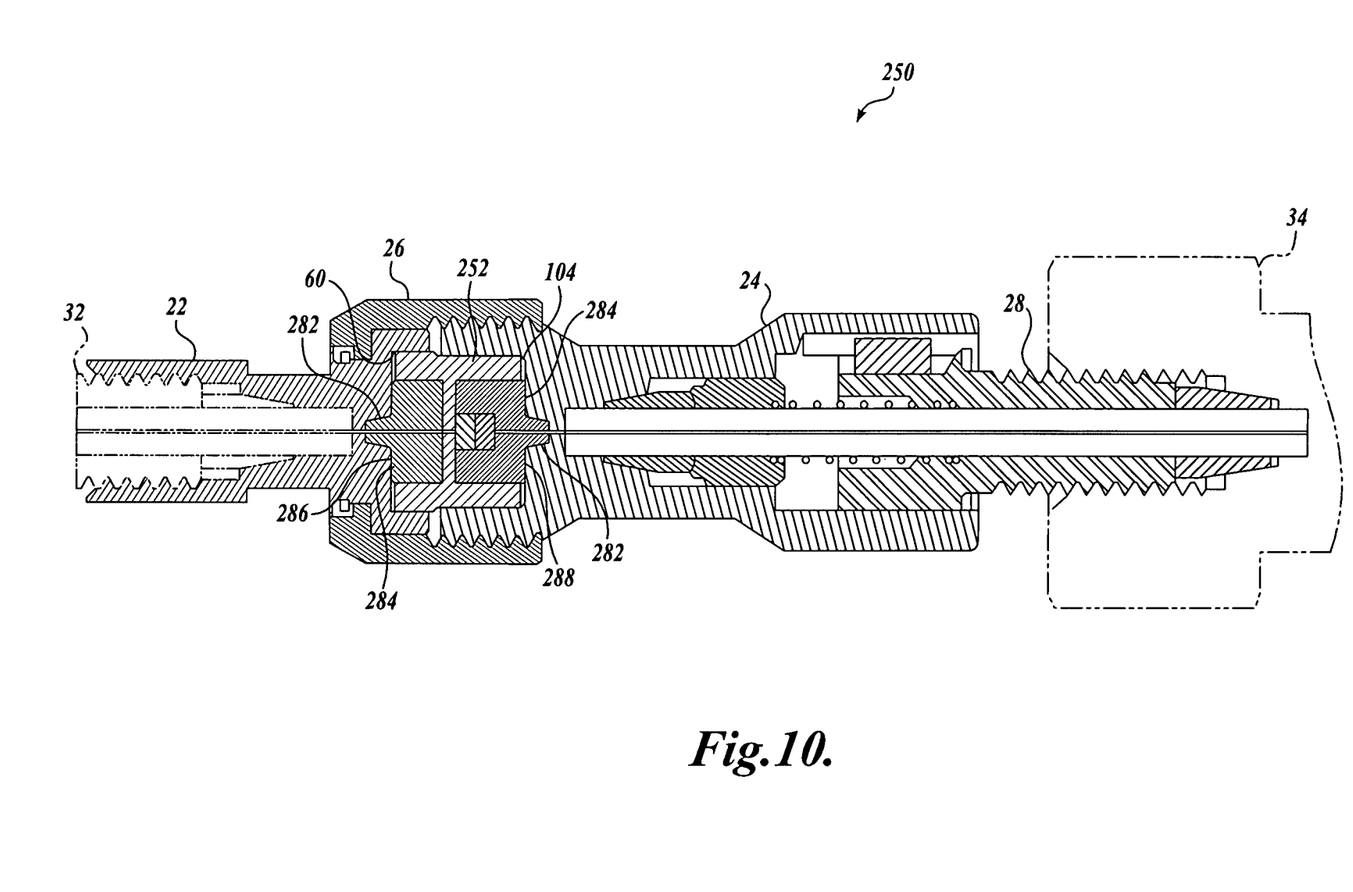
FIG. 10 is a cross-sectional view of an alternate embodiment of a high pressure connect fitting according to the present disclosure.
Figure 11:
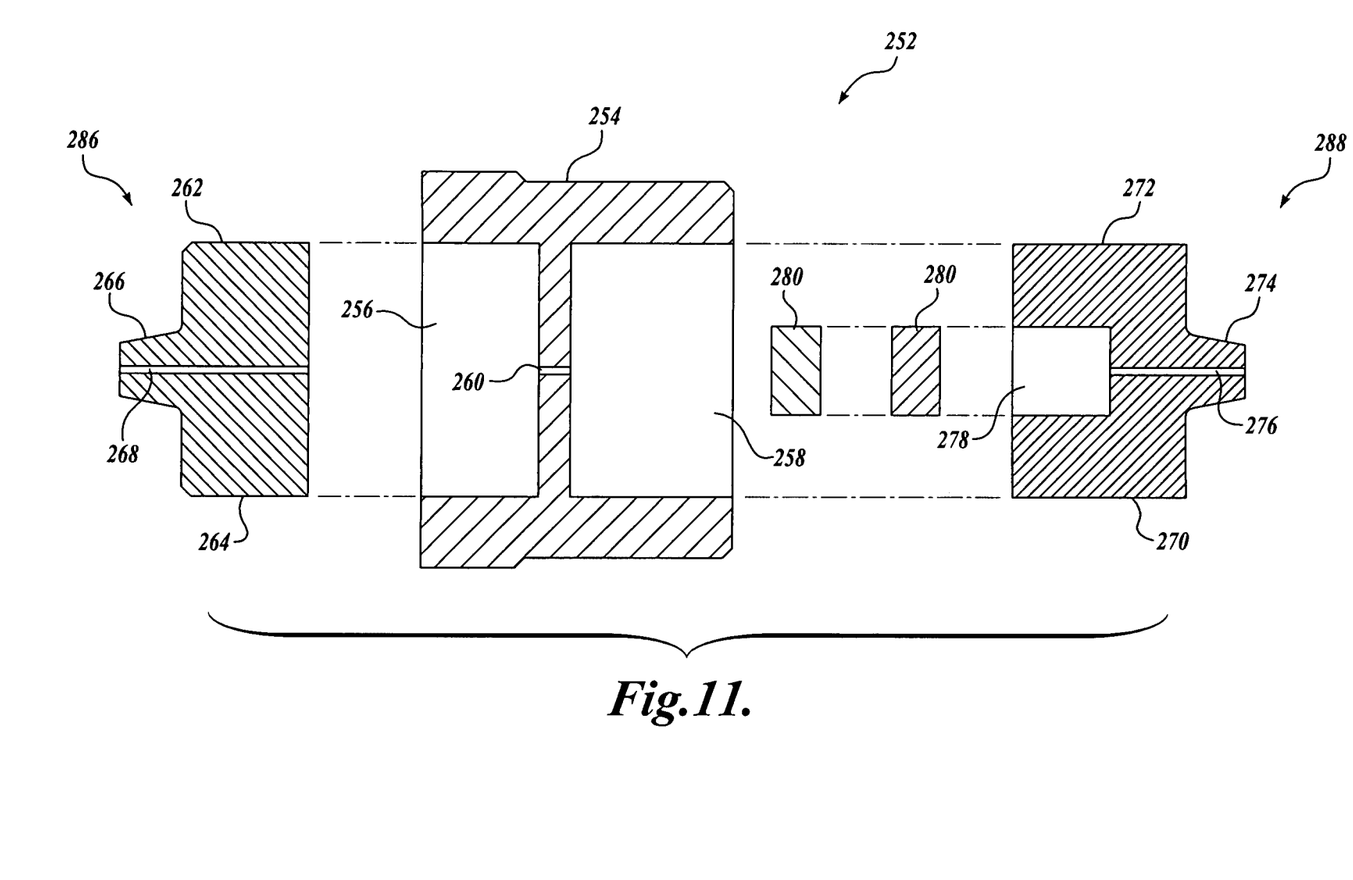
FIG. 11 is an exploded cross-sectional view of a filter cartridge of the high pressure connect fitting shown in FIG. 10.

An alternate embodiment of the disclosed high pressure connect fitting is illustrated in FIGS. 10 and 11. The high pressure connect fitting 250 shown in FIG. 10 is similar to the high pressure connect fitting 20 shown in FIG. 2, except that the packed bed 30 of the previously described fitting 20 is replaced with a unidirectional filter cartridge 252. The unidirectional filter cartridge 252 includes an inlet end 286, which is positioned within the annular recess 60 of the first fitting 22, and a discharge end 288, which is positioned within the annular recess 104 of the second fitting 24.

As best shown in FIG. 11, the unidirectional filter cartridge 252 includes a generally cylindrical body 254 with a first annular recess 256 at the inlet end 286 opposed by a second annular recess 258 at the discharge end 288. The first and second annular recesses 256 and 258 are connected by a passage 256 extending through the body 254.

The diameter of the filter cartridge 252 is greater at the inlet end 286 than at the discharge end 288. As shown in FIG. 12, the diameter of the annular recess 104 in the second fitting 24 is larger than the diameter of the discharge end 288 of the filter cartridge 252, but smaller than the diameter of the inlet end 286 of the filter cartridge 252. As a result, the inlet end 286 of the filter cartridge 252 can not be inserted into the annular recess 104 of the second fitting 24. Consequently, the unidirectional filter cartridge 252 can only be installed in the high pressure connect fitting 250 in one orientation, i.e. with the inlet end 286 disposed within the first fitting 22, and the discharge end 288 disposed within the second fitting 24. It should be appreciated that various other configurations can be employed to ensure proper orientation of the filter cartridge 252, such as, for example, having the larger diameter at the outlet end of the cartridge or having different cross-sectional profiles at each end of the filter cartridge.

A first seal 262 is similar to the seal 220 of the previously described embodiment. The first seal 262 has generally cylindrical body 264, with a tip 266 on one side and a central passage 268 extending therethrough. The first seal 262 is preferably manufactured from a polymer, such as PEEK. The first seal 262 is disposed within the first annular recess 256 of the body 254 of the filter cartridge 252.

A second seal 270 is similar to the first seal 262, having a generally cylindrical body 272, a tip 274, and a passage 276 extending therethrough. However, the second seal 270 further includes an annular recess 278 opposite the tip 274. The annular recess 278 is sized and configured to receive one or more filter elements 280. Each filter element may be formed from a particulate filter material, through which particles greater than a predetermined size are prevented from passing, or a chemical filter material, such as a selectively absorbent or adsorbent material that selectively filters out substances having particular chemical properties. It should be appreciated that any known filter element suitable for selectively filtering fluids passing therethrough can be included without departing from the scope of the disclosure.

With one or more filter elements 280 positioned in the annular recess 278 of the second seal 270, the second seal 270 is received into the second annular recess 258 of the body 254 of the filter cartridge 252.

When the filter cartridge 252 is installed in the high pressure connect fitting 250, first seal 262 forms a primary seal 282 and a secondary seal 284 with the first fitting 22. Similarly, the second seal 270 forms a primary seal 282 and a secondary seal 284 with the second fitting 24. As a result, fluid passing through the high pressure connect fitting passes through the filter cartridge 252 and is filtered by the filter elements 280 contained therein.

While illustrative embodiments have been illustrated and described, it will be appreciated that various changes can be made therein without departing from the spirit and scope of the invention.

The embodiments of the invention in which an exclusive property or privilege is claimed are defined as follows:

1. An analytical instrument fitting assembly for coupling first and second analytical fluid conduits, the fitting assembly comprising:
   (a) a first fitting defining a central passage adapted to receive a first fluid conduit defining an internal diameter of no greater than 0.040 inch;
   (b) a second fitting defining a central passage extending between first and second ends and is in fluid communication with the first fitting;
   (c) a coupler releasably connecting the first and second fittings by application of a coupling force to the coupler, wherein the coupling force is substantially within a range of 0.1-5.0 inch-pounds;

(d) a separation device disposed within the central passages of the first and second fittings to selectively separate liquids passing therethrough;
(e) a retractable end fitting at least partially disposed within the second end of the second fitting, the retractable end fitting having:
  (i) a housing,
  (ii) a tube extending within the housing; and
  (iii) a biasing member extending between the housing and a washer slidably disposed on the tube, wherein the washer is movable relative to the housing to allow selective positioning of the tube within the housing relative to the second end of the second fitting to minimize dead space between the tube and the second end of the second fitting; and
(f) a restraint slidingly engaging at least one of the second fitting and the housing to prevent rotation of the housing relative to the second fitting, wherein movement of the housing relative to the second fitting is limited to a longitudinal direction.

2. The fitting assembly of claim 1, wherein the separation device comprises a packed bed, the packed bed including:
  (i) a body at least partially filled with a separating media; and
  (ii) a first seal disposed on a first end of the body to seal the separating media within the body.

3. The fitting assembly of claim 2, wherein the packed bed further comprises a second seal disposed on a second end of the body, the first and second seals each having a tip portion of a pliable material, wherein the first and second tips are deformable to define secondary sealing surfaces between the tip portions and corresponding sealing surfaces of the first and second fittings, respectively.

4. The fitting assembly of claim 1, wherein the biasing member is a spring.

5. The fitting assembly of claim 1, wherein the fitting assembly is in substantially zero-dead volume communication with a second fluid conduit when the fitting assembly is coupled to the second fluid conduit.

6. The fitting assembly of claim 1, wherein the restraint comprises a pin having a longitudinal axis substantially parallel to a longitudinal axis of the tube.

7. The fitting assembly of claim 1, wherein the coupler is a lock ring adapted to rotatably couple the first fitting to the second fitting.

8. The fitting assembly of claim 7, wherein the coupler rotatably couples the first and second fittings by application of substantially between 0.5 and 2.0 inch pounds of coupling force to the coupler to cause the coupler to rotate substantially between 45°-60° from an unlocked position.

9. The fitting assembly of claim 7, wherein the lock ring is rotatably coupled to the first fitting and threadedly coupled to the second fitting.

10. The fitting assembly of claim 1, wherein the separation device comprises a filter cartridge, the filter cartridge including:
  (i) a body at least partially filled with a separating media; and
  (ii) a first seal disposed on a first end of the body to seal the separating media within the body.

11. The fitting assembly of claim 10, wherein the filter cartridge includes a second seal disposed on a second end of the body, the first and second seals each having a tip portion of a pliable material, wherein the first and second tips are deformable to define secondary sealing surfaces between the tip portions and corresponding sealing surfaces of the first and second fittings, respectively.

12. The fitting assembly of claim 11, wherein the filter cartridge may be disposed within the central passages of the first and second fittings in only one direction.

13. An analytical instrument fitting assembly fitting assembly for coupling first and second analytical fluid conduits, the fitting assembly comprising:
(a) a first fitting defining a central passage adapted to receive a first fluid conduit defining an internal diameter of no greater than 0.040 inch;
(b) a second fitting defining a central passage extending between first and second ends and is in fluid communication with the first fitting;
(c) a separation device disposed within the central passages of the first and second fittings to selectively separate liquids passing therethrough;
(d) a retractable end fitting at least partially disposed within the second end of the second fitting, the retractable end fitting having:
  (i) a housing;
  (ii) a tube extending within the housing, the tube having a first end in fluid communication with the first fitting and a second end adapted to receive a second fluid conduit defining an internal diameter of no greater than 0.040 inch; and
  (iii) a biasing member extending between the housing and a washer slidably disposed on the tube, wherein the washer is movable relative to the housing to allow selective positioning of the tube within the housing relative to the second end of the second fitting to minimize dead space between the tube and the second end of the second fitting; and
(f) a restraint slidingly engaging at least one of the second fitting and the housing to prevent rotation of the housing relative to the second fitting, wherein the restraint limits movement of the housing relative to the second fitting to a longitudinal direction.

14. The fitting assembly of claim 13, wherein the separation device comprises a packed bed disposed within the central passages of the first and second fittings, the packed bed including:
  (i) a body at least partially filled with a separating media; and
  (ii) a first seal disposed on a first end of the body to seal the separating media within the body.

15. The fitting assembly of claim 13, wherein the separation device comprises a filter cartridge disposed within the central passages of the first and second fittings.

16. The fitting assembly of claim 15, wherein the filter cartridge includes:
  (a) a body having an inlet end and a discharge end;
  (b) first and second seals adapted to fit within the inlet and discharge ends, respectively; and
  (c) a filter element disposed within the body.

17. The fitting assembly of claim 16, wherein the filter cartridge is configured to be disposed within the central passages of the first and second fittings in only one direction.

18. The fitting assembly of claim 13, wherein the fitting assembly is in substantially zero-dead volume communication with the second fluid conduit when the fitting assembly is coupled to the second fluid conduit.

19. The fitting assembly of claim 13, wherein the restraint comprises a pin having a longitudinal axis substantially parallel to a longitudinal axis of the tube.

20. The fitting assembly of claim 13, wherein the biasing member is a helical spring disposed coaxially around the tube.

21. The fitting assembly of claim 13, further comprising a coupler releasably connecting the first and second fittings by application of a coupling force to the coupler, wherein the coupling force is substantially within a range of 0.1-5.0 inch-pounds.

22. The fitting assembly of claim 21, wherein the coupler rotatably couples the first and second fittings by application of substantially between 0.5 and 2.0 inch pounds of coupling force to the coupler to cause the coupler to rotate substantially between 45°-60° from an unlocked position.

23. The fitting assembly of claim 21, wherein the separation device comprises a packed bed disposed within the central passages of the first and second fittings, the packed bed including:
 (i) a body at least partially filled with a separating media and
 (ii) a first seal disposed on a first end of the body to seal the separating media within the body.

\* \* \* \* \*